United States Patent
Narayanan

(10) Patent No.: US 6,884,285 B2
(45) Date of Patent: Apr. 26, 2005

(54) DELIVERY SYSTEM FOR WOOD TREATMENT CHEMICALS

(75) Inventor: Kolazi S. Narayanan, Wayne, NJ (US)

(73) Assignee: ISP Investments Inc., Wilmington, DE (US)

(*) Notice: Subject to any disclaimer, the term of this patent is extended or adjusted under 35 U.S.C. 154(b) by 87 days.

(21) Appl. No.: 10/456,307

(22) Filed: Jun. 6, 2003

(65) Prior Publication Data

US 2004/0244639 A1 Dec. 9, 2004

(51) Int. Cl.⁷ .................. A01N 31/00; A01N 31/10; A01N 31/12
(52) U.S. Cl. ................. 106/18.32; 106/15.05; 106/18.31; 106/18.33; 424/405; 514/222.8; 514/731
(58) Field of Search .............. 106/15.05, 18.31, 106/18.32, 18.33; 424/405; 514/222.8, 731

(56) References Cited

U.S. PATENT DOCUMENTS

| | | | | |
|---|---|---|---|---|
| 5,300,529 A | * | 4/1994 | Narayanan | 514/788 |
| 5,317,042 A | * | 5/1994 | Narayanan | 514/772 |
| 5,968,990 A | * | 10/1999 | Jon et al. | 514/788 |
| 6,033,681 A | * | 3/2000 | Narayanan et al. | 424/405 |
| 6,045,816 A | * | 4/2000 | Narayanan et al. | 424/405 |
| 6,506,396 B1 | * | 1/2003 | Narayanan et al. | 424/405 |

OTHER PUBLICATIONS

Internet article from ISP Agrochemicals entitled "Microflex" http://www.ispcorp.com/products/agchem/content/formulations/micro (2003), no month.*

Internet article from ISP Household and Specialites entitled "Dispersants, Emulsifiers & Specialties" http://www.ispcorp.com/products/housespec/content/products/microf. (2003), no month.*

Bethoxazin data sheet from the Compendium of Pesticide Common Names http://www.hclrss.demon.co.uk/bethoxazin.html, no date.*

* cited by examiner

*Primary Examiner*—Anthony J. Green
(74) *Attorney, Agent, or Firm*—William J. Davis; Walter Katz

(57) ABSTRACT

A wood treatment concentrate includes, by weight;
(a) 0.1–10% of an active wood treatment chemical,
(b) 50–99% of a microemulsion concentrate including:
  (i) 0.03–80%, preferably 40–70%, of a castor oil ethoxylate or tristyryl phenol ethoxylate,
  (ii) 0–10%, preferably 0.005–6%, of an ethoxylated phosphoric acid ester as pH buffer,
  (iii) 0.002–40%, preferably 0.05–29%, of a $N$—$C_8$–$C_{18}$ alkyl pyrrolidone and
  (iv) 0–60%, preferably 0.15–40%, of a $N$—$C_1$–$C_4$ alkyl pyrrolidone, and
  (v) 0–30%, preferably 0.5–15%, of an ethylene oxide/propylene oxide block copolymer; and
(c) 1–50% of a substituted phenol.

The use formulation includes (d) water of dilution.

8 Claims, No Drawings

DELIVERY SYSTEM FOR WOOD TREATMENT CHEMICALS

BACKGROUND OF THE INVENTION

1. Field of the Invention

This invention relates to wood treatment concentrates, and, more particularly, to a stable, aqueous wood treatment formulation containing a high loading of an active wood treatment chemical.

2. Description of the Prior Art

K. Narayanan, in U.S. Pat. No. 6,045,816, described a water-based microemulsion (Microflex®) of an active pyrethroid insecticide for delivery of the active at a high loading to treat fruits and vegetable crops. In this invention, there is provided a stable aqueous wood treatment concentrate and use formulation which includes Microflex® modified by including therein a substituted phenol therein. This modified Microflex® is particularly useful for treating and preserving wood by contacting it with a high loading of the active wood treatment chemical.

SUMMARY OF THE INVENTION

What is described herein is a wood treatment concentrate which includes, by weight;

(a) 0.1–10%, preferably 0.5–5%, of an active wood treatment chemical, e.g. bethoxazin,
(b) 50–99%, preferably 60–95%, of a microemulsion concentrate including:
  (i) 0.03–80%, preferably 40–70%, of a castor oil ethoxylate or tristyryl phenol ethoxylate,
  (ii) 0–10%, preferably 0.005–6%, of an ethoxylated phosphoric acid ester as pH buffer,
  (iii) 0.002–40%, preferably 0.05–29%, of a N—$C_8$–$C_{18}$ alkyl pyrrolidone and
  (iv) 0–60%, preferably 0.15–40%, of a N—$C_1$–$C_4$ alkyl pyrrolidone, and
  (v) 0–30%, preferably 0.5–15%, of an ethylene oxide/propylene oxide block copolymer; and
(c) 1–50%, preferably 5–40%, of a substituted phenol.

The use formulation includes (d) water of dilution, e.g. 1:10 to 1:1000, preferably 1:20 to 1:100.

In a preferred form of the invention, (a) forms a molecular complex with (c).

The substituted phenol (c) is preferably thymol, cresol, hexachlorophene, methylene bis 2,6, dichlorophenol, dichlorophene, 2,4, dichloro 3,5, dimethyl phenol (DCMX), xylenol, chloro xylenols, 4-benzyl 2-chloro 6-methyl phenol, 5-chloro-2-hydroxy biphenyl, chlorophene, p-chloro m-cresol, methoxy phenol, ethoxy phenol, isopropoxy phenol and/or pentachlorophenol.

DETAILED DESCRIPTION OF THE INVENTION

In this invention, the wood preservation concentrate is referred to hereinafter as MICROFLEX®-1. More particularly, MICROFLEX®-1 includes, by weight;

(a) 0.1–10%, preferably 0.5–5%, of an active wood treatment chemical, e.g. bethoxazin;
(b) 50–99%, preferably 60–95%, of a microemulsion concentrate including:
  (i) 0.03–80%, preferably 40–70%, of a castor oil ethoxylate or tristyryl phenol ethoxylate,
  (ii) 0–10%, preferably 0.005–6%, of an ethoxylated phosphoric acid ester as pH buffer,
  (iii) 0.002–40%, preferably 0.05–29%, of a N—$C_8$–$C_{18}$ alkyl pyrrolidone and
  (iv) 0–60%, preferably 0.15–40%, of a N—$C_1$–$C_4$ alkyl pyrrolidone, and
  (v) 0–30%, preferably 0.5–15%, of an ethylene oxide/propylene oxide block copolymer, and
(c) 1–50%, preferably 5–40%, of a substituted phenol.

The use formulation includes (d) water of dilution, e.g. 1:10 to 1:1000, preferably 1:20 to 1:100.

Preferably, the substituted phenol is a liquid phenol, or easily liquifiable, e.g. a low melting point, most preferably, less than 60° C. Substituted phenolics with anti-microbial activity also can act as a solubilizer and biocide at the same time, e.g. thymol, cresol, hexachlorophene, methylene bis 2,6, dichlorophenol, dichlorophene, 2,4, dichloro 3,5, dimethyl phenol (DCMX), xylenol, chloro xylenols, 4-benzyl 2-chloro 6-methyl phenol, 5-chloro-2-hydroxy biphenyl, chlorophene, p-chloro m-cresol, methoxy phenol, ethoxy phenol, isopropoxy phenol and pentachlorophenol.

Accordingly, the invention compositions herein contain substituted phenols in combination with the components of Microflex®, which, upon dilution with water, form stable microemulsions. This modified Microflex® composition enables the composition to retain a high loading of wood treatment chemicals, preferably by forming a molecular complex with the substituted phenol component.

A typical invention wood treatment concentrate of Microflex® and substituted phenol (thymol), before addition of the wood treatment chemical and water, is shown below:

TABLE

| Microflex ® | Thymol |
|---|---|
| 100 | 0 |
| 90 | 10 |
| 80 | 20 |
| 70 | 30 |
| 60 | 40 |
| 50 | 50 |

This concentrate matrix was used with a mixture of actives including bethoxazin within the range of 0.1–10% total active. The concentrates were diluted with water at a 1/40 dilution. Both the concentrate and use formulations was free from crystal separation of actives.

While the invention has been described with particular reference to certain embodiments thereof, it will be understood that changes and modifications may be made which are within the skill of the art. Accordingly, it is intended to be bound only by the following claims, in which:

What is claimed is:

1. A wood treatment concentrate includes, by weight;

(a) 0.1–10% of an active wood treatment chemical,
(b) 50–99% of a microemulsion concentrate including:
  (i) 0.03–80% of a castor oil ethoxylate or tristyryl phenol ethoxylate,
  (ii) 0–10% of an ethoxylated phosphoric acid as pH buffer,
  (iii) 0.002–40% of a N—$C_8$–$C_{18}$ alkyl pyrrolidone and
  (iv) 0–60% of a N—$C_1$–$C_4$ alkyl pyrrolidone, and
  (v) 0–30% of an ethylene oxide/propylene oxide block copolymer, and
(c) 1–50% of a substituted phenol.

2. A wood treatment concentrate according to claim 1 wherein (i) is 40–70%, (ii) is 0.005–6%, (iii) is 0.05–29%, (iv) is 0.15–40% and (v) is 0.5–15%.

3. A wood treatment concentrate according to claim 1 wherein (a) forms a molecular complex with (c).

4. A concentrate according to claim 1 wherein (a) is 0.5–5%; (b) is 60–95%, and (c) is 5–40%.

5. A concentrate according to claim 1 wherein (c) is selected from the group consisting of thymol, cresol, hexachlorophene, methylene bis 2,6, dichlorophenol, dichlorophene, 2,4,dichloro 3,5, dimethyl phenol (DCMX), xylenol, chloro xylenols, 4-benzyl 2-chloro 6-methyl phenol, 5-chloro-2-hydroxy biphenyl, chlorophene, p-chloro m-cresol, methoxy phenol, ethoxy phenol, isopropoxy phenol and pentachlorophenol.

6. A concentrate according to claim 1 wherein (a) includes bethoxazin.

7. A formulation of the concentrate of claim 1 and (d) water of dilution at a dilution ratio of 1:10 to 1:1000.

8. A formulation according to claim 7 at a dilution ratio of 1:20 to 1:100.

* * * * *